United States Patent
Wittnebel

(10) Patent No.: US 11,197,781 B2
(45) Date of Patent: Dec. 14, 2021

(54) LASER PULSE MODULATION FOR LASER CORNEAL TREATMENTS

(71) Applicant: Alcon Inc., Fribourg (CH)

(72) Inventor: Michael Wittnebel, Hirschaid (DE)

(73) Assignee: Alcon Inc., Fribourg (CH)

( * ) Notice: Subject to any disclaimer, the term of this patent is extended or adjusted under 35 U.S.C. 154(b) by 331 days.

(21) Appl. No.: 16/148,931

(22) Filed: Oct. 1, 2018

(65) Prior Publication Data
US 2019/0110921 A1     Apr. 18, 2019

Related U.S. Application Data

(60) Provisional application No. 62/571,940, filed on Oct. 13, 2017.

(51) Int. Cl.
*A61F 9/008* (2006.01)

(52) U.S. Cl.
CPC .......... *A61F 9/008* (2013.01); *A61F 9/00802* (2013.01); *A61F 9/00825* (2013.01); *A61F 2009/00844* (2013.01); *A61F 2009/00853* (2013.01); *A61F 2009/00872* (2013.01); *A61F 2009/00878* (2013.01); *A61F 2009/00897* (2013.01)

(58) Field of Classification Search
CPC ............ A61F 2009/00872; A61F 9/008; A61F 2009/00897; A61F 9/00836; A61F 2007/0004; A61F 7/007; A61B 2017/00508; A61B 2017/00517
See application file for complete search history.

(56) References Cited

U.S. PATENT DOCUMENTS

| | | | |
|---|---|---|---|
| 5,779,696 A | 7/1998 | Berry et al. | |
| 2005/0024586 A1* | 2/2005 | Teiwes | A61F 9/008 351/209 |
| 2007/0135805 A1 | 6/2007 | Peyman | |
| 2010/0241108 A1 | 9/2010 | Wuellner | |
| 2011/0238046 A1 | 9/2011 | Dick et al. | |
| 2012/0150160 A1* | 6/2012 | Vogler | A61F 9/008 606/4 |
| 2012/0296318 A1 | 11/2012 | Wellhoefer et al. | |
| 2014/0276678 A1 | 9/2014 | Berry et al. | |
| 2016/0250074 A1 | 9/2016 | Fu | |
| 2017/0304119 A1 | 10/2017 | Yee | |
| 2018/0078412 A1 | 3/2018 | Luttrull et al. | |

FOREIGN PATENT DOCUMENTS

| | | |
|---|---|---|
| CN | 1957867 A | 5/2007 |
| CN | 101732127 A | 6/2010 |
| EP | 1702595 B1 | 12/2010 |
| WO | 2011/015205 A1 | 2/2011 |

\* cited by examiner

*Primary Examiner* — Jon Eric C Morales

(57) ABSTRACT

Laser pulse modulation for laser corneal treatments is used to control the thermal energy imparted to the cornea. The optical energy of the laser pulses may be modulated to reduce or increase the thermal energy, depending upon an expected thermal load or a measured temperature at each position location of the cornea subject to laser treatment. The laser pulse modulation may involve pulse frequency modulation, pulse amplitude modulation, and pulse duration modulation.

20 Claims, 4 Drawing Sheets

METHOD FOR LASER PULSE MODULATION

500

502 — ACCESSING A SURGICAL PLAN FOR A CORNEAL LASER TREATMENT OF A CORNEA OF A PATIENT, WHERE THE SURGICAL PLAN SPECIFIES POSITION LOCATIONS ON THE CORNEA FOR THE CORNEAL LASER TREATMENT AND A NUMBER OF LASER PULSES FOR EACH OF THE POSITION LOCATIONS

504 — PERFORMING THE CORNEAL LASER TREATMENT ACCORDING TO THE SURGICAL PLAN, WHERE A THERMAL ENERGY IMPARTED TO A FIRST POSITION LOCATION ON THE CORNEA BY THE LASER PULSES IS CONTROLLED BY MODULATING AN OPTICAL ENERGY OF THE LASER PULSES AT THE FIRST POSITION LOCATION TO CONTROL A TEMPERATURE OF THE CORNEA

FIG. 5

LASER PULSE MODULATION FOR LASER CORNEAL TREATMENTS

BACKGROUND

Field of the Disclosure

The present disclosure relates to ophthalmic surgery, and more specifically, to laser pulse modulation for laser corneal treatments.

Description of the Related Art

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple spherical and cylindrical errors that cause myopia, hyperopia, or regular astigmatism, to more complex refractive errors that can cause, for example, halos and starbursts in a person's vision.

Many interventions have been developed over the years to correct various ocular aberrations. These include spectacles, contact lenses, corneal implants, intraocular lenses (IOLs), as well as laser corneal treatments in the form of corneal refractive surgery, such as laser-assisted in situ keratomileusis (LASIK) or transepithelial photorefractive keratectomy (T-PRK). In particular, laser corneal treatments may involve a high number of laser pulses directed at the cornea, which may cause undesired thermal energy to be imparted to the cornea and may raise the temperature of the cornea.

SUMMARY

In one aspect, a disclosed method is for laser pulse modulation for corneal laser treatments. The method may include accessing a surgical plan for a corneal laser treatment of a cornea of a patient. In the method, the surgical plan may specify position locations on the cornea for the corneal laser treatment and a number of laser pulses for each of the position locations. The method may further include performing the corneal laser treatment according to the surgical plan. In the method, a thermal energy imparted to a first position location on the cornea by the laser pulses may be controlled by modulating an optical energy of the laser pulses at the first position location to control a temperature of the cornea.

In any of the disclosed embodiments of the method, modulating the optical energy may further include modulating a frequency of the laser pulses.

In any of the disclosed embodiments of the method, modulating the optical energy may further include modulating at least one of an amplitude and a duty cycle of the laser pulses.

In any of the disclosed embodiments of the method, modulating the optical energy may further include linearly reducing the optical energy of the laser pulses at the first position location from a rated value of a laser source used for the corneal laser treatment to a second value lower than the rated value over a duration. In the method, the second value and the duration may be predetermined to limit the thermal energy to prevent the temperature of the cornea at the first position location from exceeding a threshold temperature.

In any of the disclosed embodiments of the method, modulating the optical energy may further include reducing the optical energy of the laser pulses at first position locations from a rated value of a laser source used for the corneal laser treatment to a second value lower than the rated value. In the method, the second value may be predetermined to limit the thermal energy imparted to the first position locations to prevent the temperature of the cornea at the first position location from exceeding a threshold temperature, while the first position locations may be specified by the surgical plan to respectively receive the number of laser pulses exceeding a threshold pulse number.

In any of the disclosed embodiments of the method, the second value may further depend upon the number of laser pulses in a specified mathematical relationship.

In any of the disclosed embodiments of the method, modulating the optical energy may further include during the corneal laser treatment, measuring a maximum temperature of the cornea, and, based on the maximum temperature of the cornea, regulating the optical energy of the laser pulses at the first position location to limit the thermal energy to prevent the maximum temperature from exceeding a threshold temperature, including reducing the optical energy when the maximum temperature exceeds the threshold temperature and increasing the optical energy when the maximum temperature does not exceed the threshold temperature.

In any of the disclosed embodiments of the method, measuring the maximum temperature of the cornea may further include measuring the maximum temperature of the stroma of the cornea.

In any of the disclosed embodiments of the method, measuring the maximum temperature of the cornea may further include using a thermal imaging device to generate temperature values correlated to the position locations, and determining whether a local temperature at the first position location exceeds the threshold temperature.

In any of the disclosed embodiments of the method, regulating the optical energy of the laser pulses at the first position location may further include regulating the optical energy based on the local temperature at the first position location, including reducing the optical energy when the local temperature exceeds the threshold temperature and increasing the optical energy when the local temperature does not exceed the threshold temperature.

In yet another aspect, a laser system for corneal laser treatments is disclosed. The laser system may include a laser source for generating laser pulses for a corneal laser treatment of a cornea of a patient, a laser scanner enabled to receive the laser pulses from the laser source and direct the laser pulses to position locations on the cornea, and a laser controller including a processor having access to memory media storing instructions executable by the processor. The instructions may be executable by the processor for accessing a surgical plan for the corneal laser treatment. In the laser system, the surgical plan may specify position locations on the cornea and a number of laser pulses for each of the position locations. The instructions may further be executable by the processor for controlling the corneal laser treatment according to the surgical plan. In the laser system, a thermal energy imparted to a first position location on the cornea by the laser pulses may be controlled by modulating an optical energy of the laser pulses at the first position location to control a temperature of the cornea.

In any of the disclosed embodiments of the laser system, modulating the optical energy may further include modulating a frequency of the laser pulses.

In any of the disclosed embodiments of the laser system, modulating the optical energy in the laser system, modulating at least one of an amplitude and a duty cycle of the laser pulses.

In any of the disclosed embodiments of the laser system, modulating the optical energy may further include linearly reducing the optical energy of the laser pulses at the first position location from a rated value of a laser source used for the corneal laser treatment to a second value lower than the rated value over a duration. In the laser system, the second value and the duration may be predetermined to limit the thermal energy to prevent the temperature of the cornea at the first position location from exceeding a threshold temperature.

In any of the disclosed embodiments of the laser system, modulating the optical energy may further include reducing the optical energy of the laser pulses at second position locations from a rated value of a laser source used for the corneal laser treatment to a second value lower than the rated value. In the laser system, the second value is predetermined to limit the thermal energy imparted to the second position locations to prevent the temperature of the cornea at the first position location from exceeding a threshold temperature, while the second position locations are specified by the surgical plan to respectively receive the number of laser pulses exceeding a threshold pulse number.

In any of the disclosed embodiments of the laser system, the second value may further depend upon the number of laser pulses in a specified mathematical relationship.

In any of the disclosed embodiments of the laser system, the laser system may further include a thermal sensor configured to monitor thermal energy of the cornea, while modulating the optical energy may further include, during the corneal laser treatment, measuring a maximum temperature of the cornea using the thermal sensor, and, based on the maximum temperature of the cornea, regulating the optical energy of the laser pulses at the first position location to limit the thermal energy to prevent the maximum temperature from exceeding a threshold temperature, including reducing the optical energy when the maximum temperature exceeds the threshold temperature and increasing the optical energy when the maximum temperature does not exceed the threshold temperature.

In any of the disclosed embodiments of the laser system, measuring the maximum temperature of the cornea may further include measuring the maximum temperature of the stroma of the cornea.

In any of the disclosed embodiments of the laser system, the thermal sensor may include a thermal imaging device, while measuring the maximum temperature of the cornea may further include using the thermal imaging device to generate temperature values correlated to the position locations, and determining whether a local temperature at the first position location exceeds the threshold temperature.

In any of the disclosed embodiments of the laser system, regulating the optical energy of the laser pulses at the first position location may further include regulating the optical energy based on the local temperature at the position location, including reducing the optical energy when the local temperature exceeds the threshold temperature and increasing the optical energy when the local temperature does not exceed the threshold temperature.

Other disclosed aspects include a laser controller for performing laser corneal treatments, the laser controller including a processor and memory accessible to the processor storing instructions executable to perform laser pulse modulation for laser corneal treatments, as disclosed herein.

BRIEF DESCRIPTION OF THE DRAWINGS

For a more complete understanding of the present invention and its features and advantages, reference is now made to the following description, taken in conjunction with the accompanying drawings, in which:

FIG. 5 is a flow chart of selected elements of a method for laser pulse modulation.

DESCRIPTION OF PARTICULAR IMPLEMENTATION(S)

Figure 1:
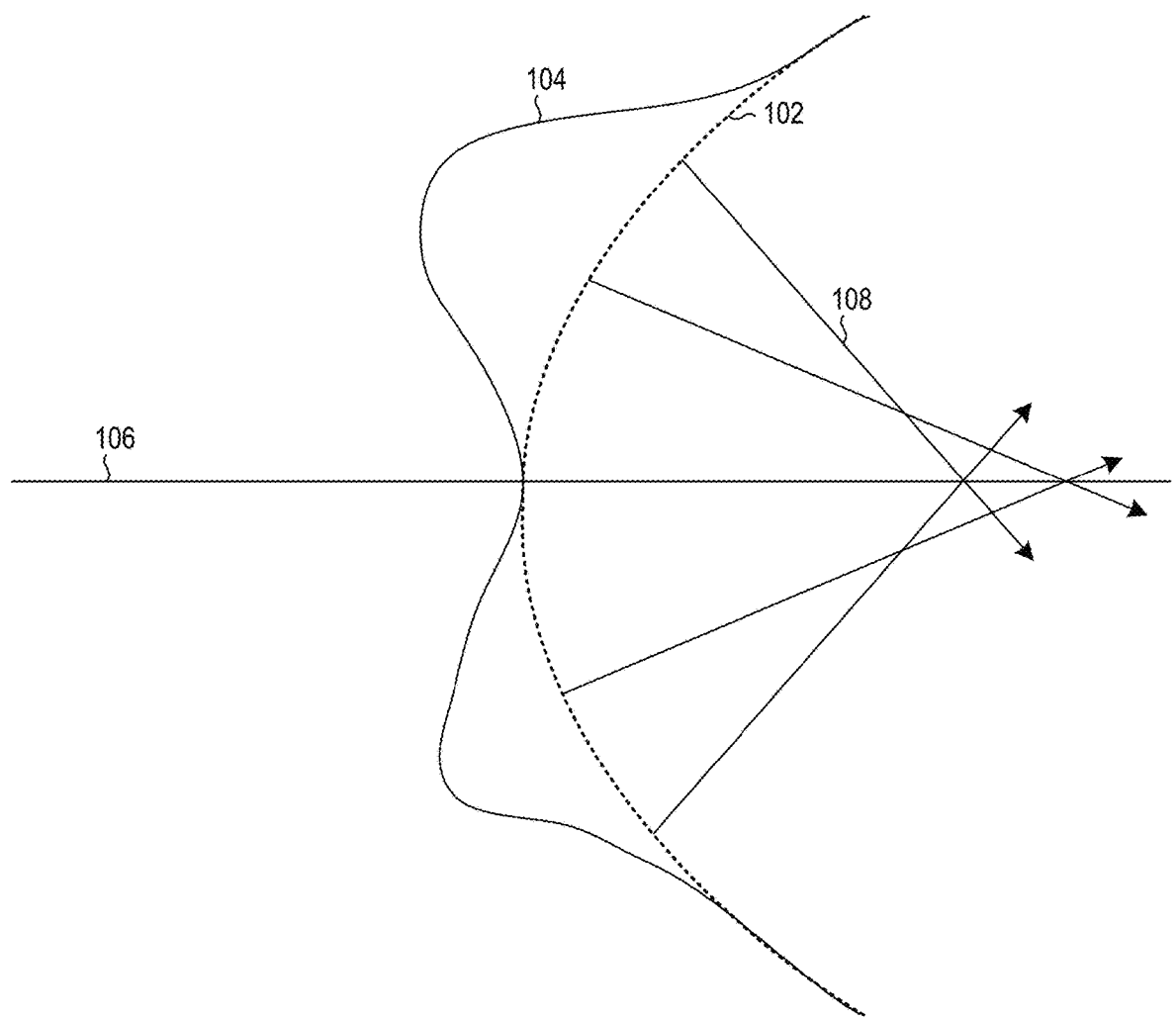
FIG. 1 is a depiction of spherical aberration of the cornea.

In the following description, details are set forth by way of example to facilitate discussion of the disclosed subject matter. It should be apparent to a person of ordinary skill in the field, however, that the disclosed implementations are exemplary and not exhaustive of all possible implementations.

Throughout this disclosure, a hyphenated form of a reference numeral refers to a specific instance of an element and the un-hyphenated form of the reference numeral refers to the element generically or collectively. Thus, as an example (not shown in the drawings), device "12-1" refers to an instance of a device class, which may be referred to collectively as devices "12" and any one of which may be referred to generically as a device "12". In the figures and the description, like numerals are intended to represent like elements.

As noted above, various laser corneal treatments have been developed to correct ocular aberrations to improve the vision of patients. The different types of laser corneal treatments may include LASIK, PRK, and T-PRK, among others. The laser systems used to perform such laser corneal treatments may include femtosecond laser systems and excimer laser systems, such as WaveLight® Allegretto Wave® and EX500, produced by Alcon Laboratories, Inc., located at 6201 South Freeway, Fort Worth, Tex. 76134. Various laser systems used to perform the laser corneal treatments may operate using different laser pulse frequencies, such as between 200 Hz and about 1,000 Hz, or higher. Typical commercial laser systems are designed to operate at a fixed value of pulse frequency or pulse power or pulse energy, which is referred to as a rated value. Each laser pulse used for laser corneal treatments may also be referred to as a 'shot' and is used to photoablate a certain amount of tissue from the surface of the cornea. The pulse frequency (or shot frequency) is typically fixed for a particular commercial laser system.

During laser corneal treatment, a continuously increasing surface temperature on the patient's eye may be observed as a result of the heat influx from the laser radiation that is provided in the form of laser pulses. When the temperature increase is too large at the surface of the eye, damage to the eye may occur as a result of the excessive thermal loading, which is undesirable. Accordingly, some conventional methods are known for reducing or limiting the heat influx to the eye during laser corneal treatments, and include using a broadly scattered and uniform distribution of individual pulses over the entire treatment surface. The uniform distribution of pulses may be algorithmically determined during the calculation of the surgical treatment plan and may prevent too many shots from being applied to the same position over a relatively long period of time. Also, the pulse frequency of the laser system may be constrained to a certain predetermined maximum frequency, such as 500 Hz, in order to limit the heat influx into the eye.

Although such conventional methods for distributing the heat influx may mitigate a local temperature increase that is too large, the conventional methods may not prevent elevated temperatures, which may occur locally near a position location of the laser surgical treatment, beyond the limits at which clinically relevant damage to the patient's eye is possible. In certain cases, cell damage may arise as a result of such excessive heating and the cell damage may cause longer recovery times or may be permanent to some extent. For example, treatments of a high refractive error of a given patient, which may involve a relatively longer laser corneal treatment time with a larger number of pulses, may be accompanied by an elevated temperature from heat influx.

As will be described in further detail, laser pulse modulation for laser corneal treatments is disclosed to control the heat influx into the patient's eye. The laser pulse modulation may be a pulse frequency modulation (shot frequency modulation), or may be a pulse amplitude/pulse duration modulation. The laser pulse modulation for laser corneal treatments disclosed herein may apply a fixed linear modulation rate during a corneal laser treatment to limit the temperature rise of the patient's eye based on predetermined factors. The laser pulse modulation for laser corneal treatments disclosed herein may implement a control loop using a temperature measurement of a treated surface of the cornea, or of a depth of the cornea, such as of the epithelium or stroma. The laser pulse modulation for laser corneal treatments disclosed herein may consider a total number of laser pulses applied to the cornea for modulating the laser pulses. The laser pulse modulation for laser corneal treatments disclosed herein may consider a local number of laser pulses applied to a particular position location of the cornea for modulating the laser pulses.

Referring now to the drawings, FIG. 1 illustrates a depiction of an implementation of a spherical aberration of the cornea 100. FIG. 1 is a schematic diagram for descriptive purposes and is not drawn to scale or perspective. In spherical aberration of the cornea 100, an optical axis 106 represents an optical axis of a human eye, while reference profile 102 may represent a spherical surface. Furthermore, anterior corneal profile 104 may represent spherical aberrations at a surface of the cornea that are shown relative to reference profile 102. For example, when performing a corneal laser treatment, anterior corneal profile 104 may depict the resulting spherical aberrations of the cornea. Also shown in FIG. 1 are rays 108, which depict how light is expected to focus along various points falling on optical axis 106. For example, the points may be selected to correspond to a location of the retina under various optical conditions to facilitate visual acuity. In this manner, anterior corneal profile 104 may be formed to create variations in refraction of incoming rays (not shown) that will result in a desired visual acuity. Although anterior corneal profile 104 is shown as a cross-sectional profile, it will be understood that circular symmetry may be applied about optical axis 106 to represent anterior corneal profile 104 in three dimensions. It is noted that anterior corneal profile 104 may further include certain asymmetric features, in various implementations.

Figure 2:
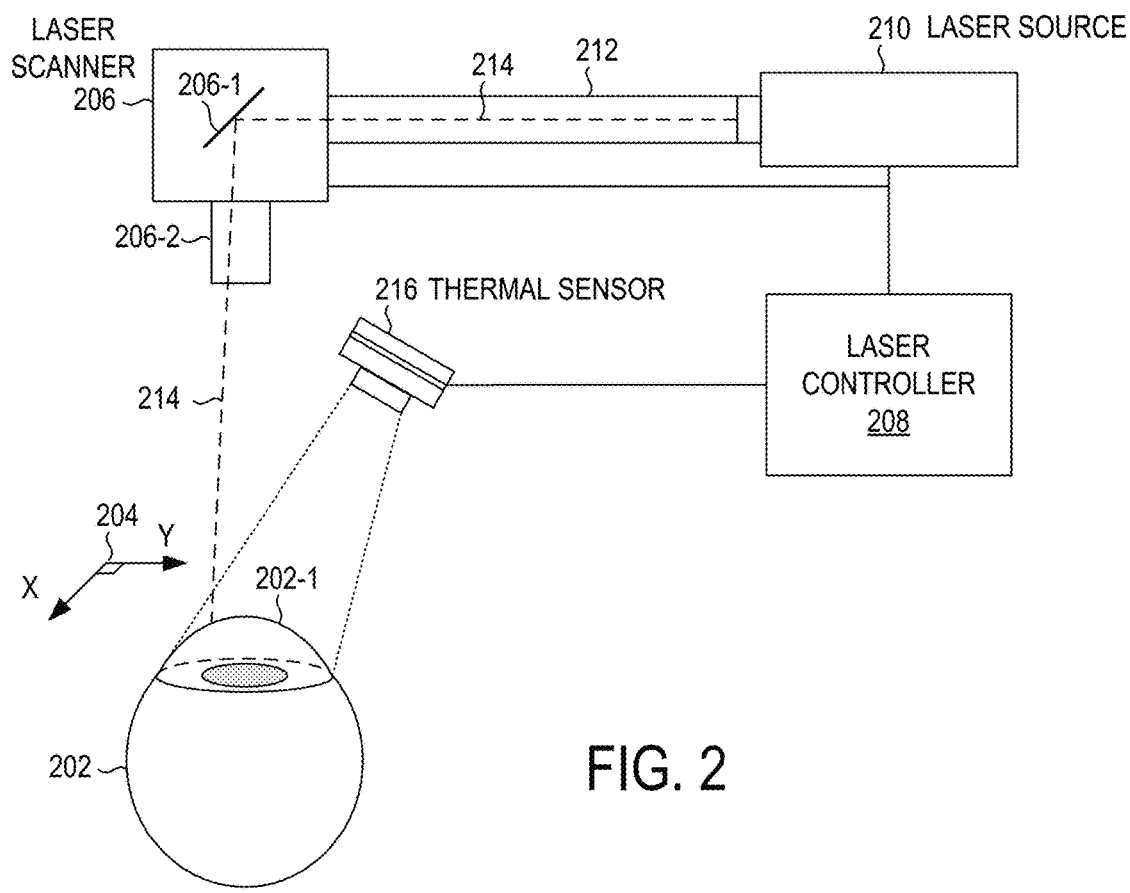
FIG. 2 is a depiction of a laser system for corneal treatments.

Referring now to FIG. 2, a depiction of an implementation of a laser system 200 for corneal treatments is shown. FIG. 2 is a schematic depiction for descriptive purposes and is not drawn to scale or perspective. It will be understood that laser system 200 may be used with fewer or more elements in different implementations.

In FIG. 2, a laser corneal treatment of an eye 202 having a cornea 202-1 is depicted. Eye 202 is representative of a patient's eye undergoing laser corneal treatment using laser system 200, which may be any of a variety of different types of laser corneal treatments. As shown, laser system 200 comprises a laser source 210 and a laser scanner 206 that may operate under control of a laser controller 208, which is described in further detail in FIG. 3. In particular implementations for laser pulse modulation for laser corneal treatments, as described herein, laser system may further include a thermal sensor 216 that can capture a temperature measurement of eye 202, and in particular, of cornea 202-1, and provide the temperature measurement to laser controller 208 to implement laser pulse modulation for laser corneal treatments.

In laser system 200, laser source 210 may represent any suitable laser source for laser pulse modulation for laser corneal treatments. For example, laser source 210 may represent an excimer laser or a femtosecond laser that operates to generate optical pulses having high intensity with relatively short duration used for laser corneal treatments. Accordingly, laser source 210 generates a laser beam 214 that may be transmitted via a beam channel 212 to laser scanner 206. At laser scanner 206, laser beam 214 is incident on laser scanner mirror 206-1, which may be used to deflect laser beam 214 in a plane, such as a plane defined by X and Y axes of a coordinate plane 204. It is noted that coordinate plane 204 is arbitrarily oriented for descriptive purposes and may be various oriented with respect to eye 202 in different implementations. It is further noted that instead of a Cartesian coordinate plane with X and Y axes, as shown in FIG. 2, coordinate plane 204 may be implemented or referenced using polar coordinates in other implementations of laser system 200, such as by using a radius R and an angle θ (not shown) to reference individual position locations on cornea 202-1. Based on position locations on cornea 202-1 that are references using coordinate plane 204, laser scanner 206 may operate to tilt laser scanner mirror 206-1 in a manner to achieve deflection of laser beam 214 according to a surgical plan that specifies a number of laser pulses for each position location on cornea 202-1. In this manner, a desired anterior cornea profile 104 (see FIG. 1) may be created on cornea 202-1 by ablation of corneal tissue as a result of the laser pulses transmitted by laser beam 214. Also shown with laser scanner 206 are beam optics 206-2, which may include various elements for collating, focusing, filtering, or other optical purposes related to laser beam 214. As shown, laser scanner 206 may be controlled by laser controller 208, which may also coordinate and control operation of laser source 210, including pulse generation and modulation, as disclosed herein.

In laser system 200, thermal sensor 216 may represent any type of optical temperature sensor that can register a temperature of cornea 202-1. For example, thermal sensor 216 may include a pyrometer or an infrared (IR) laser temperature sensor for measuring temperature at a particular position location or over the entire surface of cornea 202-1 at once. In other implementations, thermal sensor 216 may include a temperature sensitive array of elements that generates a thermal image with a given resolution. In this manner, thermal sensor 216 may operate to generate a plurality of simultaneous temperature measurements that are indexed to a corresponding plurality of position locations on cornea 202-1. It is noted that when thermal sensor 216 generates a thermal image, the imaged field comprising the plurality of position locations on cornea 202-1 may be calibrated with the position locations references by laser scanner 206 corresponding to position locations in the surgical plan for cornea 202-1. Thermal sensor 216 may be controlled by laser controller 208, such as for triggering or communicating a temperature measurement from thermal sensor 216 to laser controller 208. Accordingly, various measurement modes may be implemented using thermal sensor 216, such as continuous measurement or measurement coordinated with the application of laser pulses in laser beam 214. In some implementations, temperature measurements using thermal sensor 216 are generated in between application of laser pulses to ascertain the thermal effects of the laser radiation applied to cornea 202-1 during laser corneal treatments.

In a basic operation of laser system 200 without the use of thermal sensor 216, a specified mathematical relationship between the number of laser pulses emitted during a laser corneal treatment and a modulation of the laser energy may be defined. For example, based on certain factors, such as pupil size, cornea thickness, and other patient information, as well as the surgical plan for the patient, among other factors, a linear reduction in the pulse frequency of the laser pulses may be subject to modulation by laser controller 208. The initial pulse frequency may be the rated pulse frequency for laser system 200, while the pulse frequency is modulated by reducing the frequency linearly with an increasing number of laser pulses or an increasing duration of the corneal laser treatment. In this manner, based on the linear rate of modulation of the pulse frequency, the surface temperature of the cornea may be kept constant or the surface temperature may be prevented from increasing too rapidly to limit heat intake into eye 202. Alternatively to laser pulse frequency modulation, the laser pulse power may be modulated, such as by varying a pulse duration or a pulse amplitude in some implementations. Variation of the pulse duration may also be referred to as duty cycle modulation. It is noted that when the pulse power is reduced, the laser energy per pulse is also reduced, which will result in a lower total treatment energy according to the original surgical plan. Therefore, when a lower laser energy per pulse is used, a total number of laser pulses may be increased to compensate for the reduced laser power and to attain the same total treatment energy as in the original surgical plan. Using this approach, laser system 200 may be enabled to complete short laser corneal treatments in a fastest possible time and still avoid undesired thermal loading of cornea 202-1. Without relying on temperature measurements, the fixed relationship between the number of laser pulses and the modulation of the laser energy may be calculated intraoperatively using a formula, or may be pre-calculated and referenced by laser controller 208 in the form of a look-up table.

In a further implementation without the use of thermal sensor 216, laser system 200 may be used for laser pulse modulation for laser corneal treatments based on a specific surgical plan for the patient. The surgical plan (see also FIG. 4) may specify different ablation depths, corresponding to different numbers of laser pulses applied, at each position location on cornea 202-1. Thus, a deeper ablation depth specifies a larger number of laser pulses at a given position location. Accordingly, laser controller 208 is able to access the exact number of laser pulses that are to be applied at each position location of cornea 202-1 for a corneal laser treatment.

Hence, the available information allows laser controller 208 to modulate the laser energy to generate a lower temperature from heat influx at given position locations on cornea 202-1. In particular, position locations that receive a larger number of laser pulses may be subject to modulation of the laser energy to reduce the thermal energy influx to cornea 202-1, while position locations that receive a smaller number of pulses may be subject to modulation of the laser energy to increase the thermal energy influx to cornea 202-1. In this manner, the modulation of the laser energy may be performed flexibly and precisely at each position location to optimize treatment time while still avoiding undesired thermal loading of cornea 202-1. As above, the pulse modulation may involve pulse frequency modulation or pulse power modulation (pulse duration/pulse amplitude).

In a temperature regulated operation of laser system 200, thermal sensor 216 may be used to monitor a surface temperature of cornea 202-1 during a laser corneal treatment. In one implementation, a maximum measured temperature of cornea 202-1 is used as a limiting factor for pulse modulation of the laser pulses applied to cornea 202-1. For example, when thermal sensor 216 is an imaging camera, the maximum measured temperature from each image may be used to control the modulation of the laser energy (pulse frequency or pulse power) of the laser pulses as the laser corneal treatment progresses. Thus, when the temperature of the cornea 202-1 exceeds a certain limit, which may be predetermined, the pulse modulation is regulated to reduce the thermal load on cornea 202-1 from the corneal laser treatment, thereby causing the temperature to stop rising further, which is desirable. In some cases, when the temperature of cornea 202-1 decreases or is below another limit, pulse modulation may be used to increase the thermal load, which also serves to accelerate the laser corneal treatment to reduce treatment time. In this manner, using a closed-loop temperature regulation of a surface temperature of cornea 202-1, the overall time for the laser corneal treatment may be optimized to be as short as possible without adverse thermal effects on cornea 202-1.

Furthermore, when thermal sensor 216 is enabled for intrastromal temperature measurements, the temperature regulated operation of laser system 200 may be used for intrastromal treatments, such as with a femtosecond laser or an ultraviolet femtosecond laser used for corneal flap incisions or lenticular incisions within cornea 202-1.

In yet a further implementation with temperature regulation, laser system 200 may be used to monitor a local temperature at specific position locations where the laser pulses are being applied, and to modulate the laser energy according to a local measured temperature. In this case, the surgical plan is used as input, which provides information on the number of laser pulses to be applied at each position location on cornea 202-1. At position locations where more laser pulses are to be applied, the pulse modulation may be performed to reduce the thermal load on eye 202, while at position locations where fewer laser pulses are to be applied, the pulse modulation may be performed to increase the thermal load on eye 202. As noted above, the measurement field of thermal sensor 216 is calibrated to the position locations in the surgical plan used by laser controller 208 and laser scanner 206 to implement monitoring and regulation based on temperature at each position location.

Figure 3:
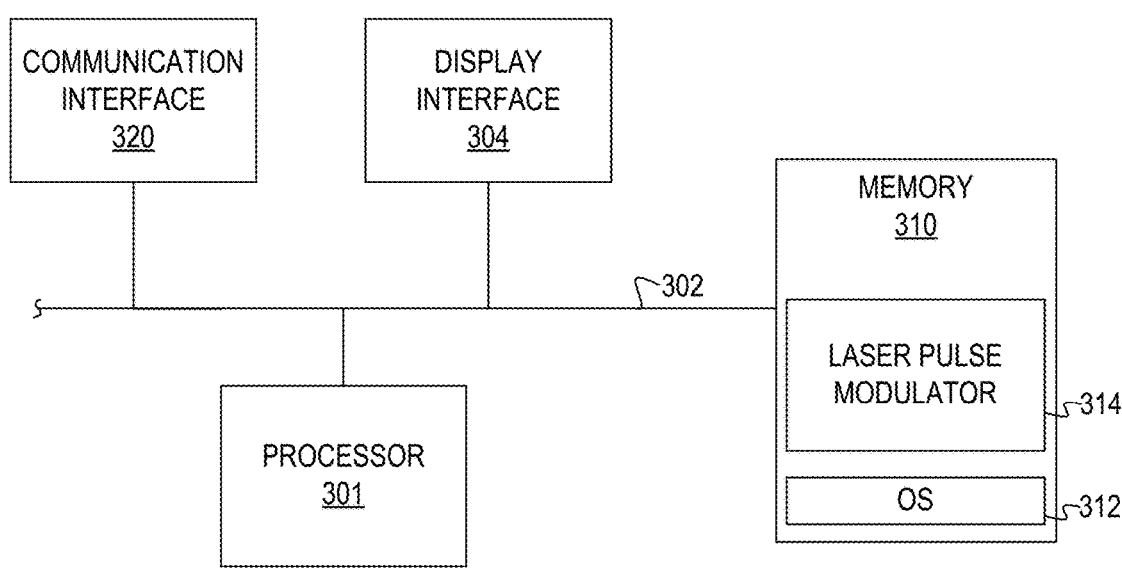
FIG. 3 is a block diagram of selected elements of a laser controller.

Referring now to FIG. 3, a block diagram illustrating selected elements of an implementation of a laser controller 300 is presented. Laser controller 300 may be enabled to perform laser pulse modulation for laser corneal treatments, as disclosed herein. In certain implementations, laser controller 300 may be integrated, or coupled to, a laser treatment system, such as laser system 200. For example, laser controller 300 may represent a particular implementation of laser controller 208 described above with respect to FIG. 2.

In the implementation depicted in FIG. 3, laser controller 300 includes processor 301 coupled via shared bus 302 to memory media collectively identified as memory 310. Laser controller 300, as depicted in FIG. 3, further includes communication interface 320 that can interface to various external entities, such as laser treatment systems, thermal sensors, laser scanners, among other devices. In some implementations, communication interface 320 is operable to enable laser controller 300 to connect to a network (not shown in FIG. 3). In implementations, as depicted in FIG. 3, laser controller 300 includes display interface 304 that connects shared bus 302, or another bus, with an output port for one or more displays. In some implementations of laser controller 300, such as with embedded implementations, the use of display interface 304 or a display may be omitted.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and a laser pulse modulator 314. Operating system 312 may be a UNIX or UNIX-like operating system, a Windows® family operating system, or another suitable operating system. Laser pulse modulator 314 may perform any of the various methods and calculations described herein for laser pulse modulation for laser corneal treatments.

Figure 4:
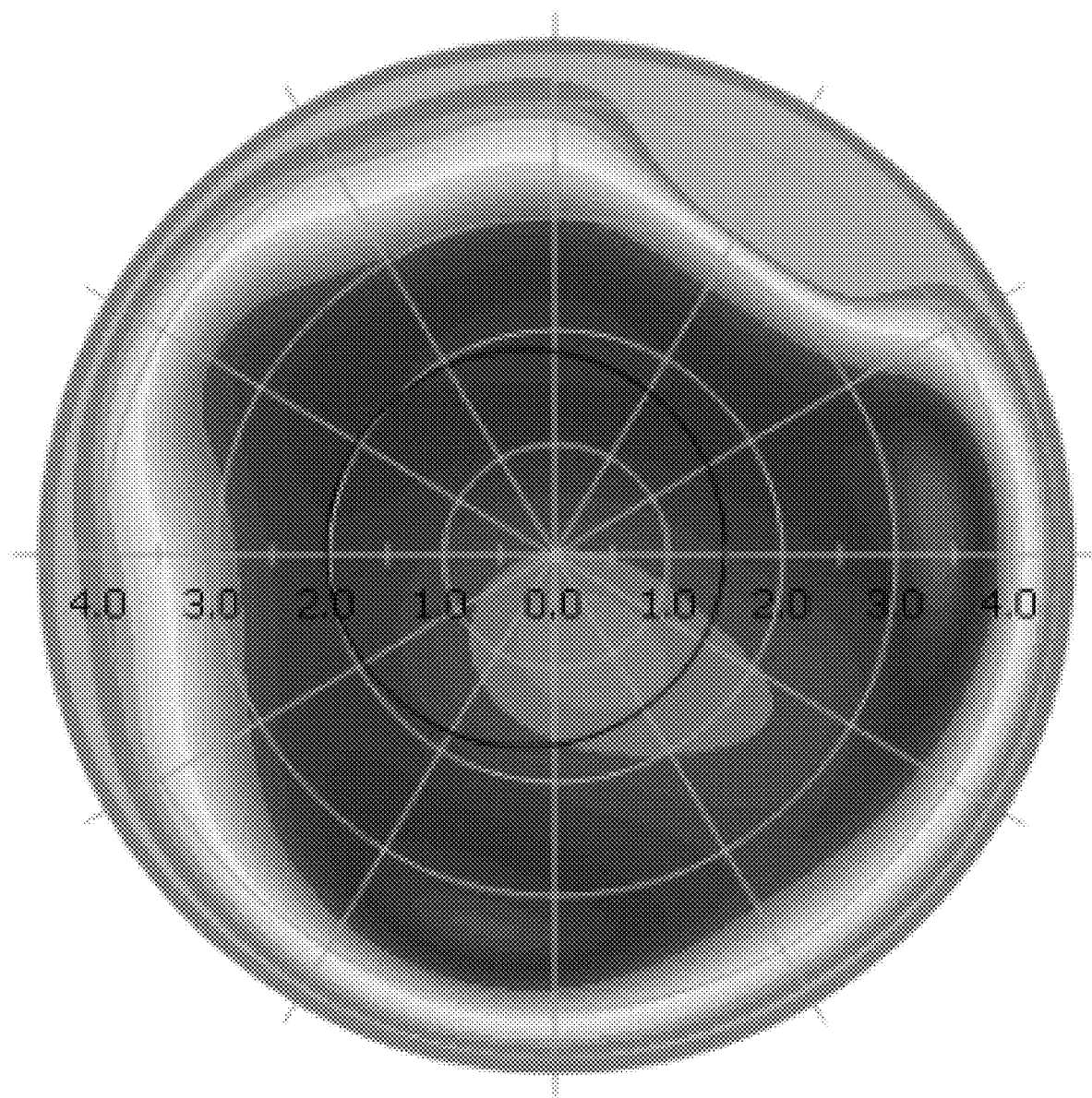
FIG. 4 is a depiction of a laser surgical plan for corneal treatments.

Referring now to FIG. 4, a surgical plan 200 for laser surgical treatments is shown as a 2-D plot. Surgical plan 200 may represent a mapping of all position locations of cornea 202-1 with an intensity value (shown unscaled in FIG. 4) at each position location that corresponds to a specific number of laser pulses to be applied at that position location. Because the number of pulses corresponds directly to the thermal loading of cornea 202-1 during the laser corneal treatment, surgical plan 200 may also be used as a temperature plan that indicates where the highest temperatures are expected to be generated when the laser corneal treatment is performed. Thus, with advance knowledge of surgical plan 200, the modulation of laser pulses at specific locations may be performed to reduce thermal loading of cornea 202-1, as described herein. Specifically, position locations having an intensity value greater than a specified value may be subject to pulse modulation to reduce the thermal loading, while position locations having an intensity value less than another specific value may be subject to pulse modulation to increase the thermal loading. As noted the pulse modulation may comprise pulse frequency modulation or pulse energy modulation (pulse duration/pulse amplitude).

Referring now to FIG. 5, a flow chart of selected elements of an implementation of a method 500 for laser pulse modulation. It is noted that certain operations described in method 500 may be optional or may be rearranged in different implementations. Method 500 may be performed using laser system 200, and specifically, by laser pulse modulator 314 in laser controller 300/208.

Method 500 may begin, at step 502, by accessing a surgical plan for a corneal laser treatment of a cornea of a patient, where the surgical plan specifies position locations on the cornea for the corneal laser treatment and a number of laser pulses for each of the position locations. At step 504, the corneal laser treatment is performed according to the surgical plan, where a thermal energy imparted to a first position location on the cornea by the laser pulses is controlled by modulating an optical energy of the laser pulses at the first position location to control a temperature of the cornea.

As disclosed herein, laser pulse modulation for laser corneal treatments is used to control the thermal energy imparted to the cornea. The optical energy of the laser pulses may be modulated to reduce or increase the thermal energy, depending upon an expected thermal load or a measured temperature at each position location of the cornea subject to laser treatment. The laser pulse modulation may involve pulse frequency modulation, pulse amplitude modulation, and pulse duration modulation.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for laser pulse modulation for corneal laser treatments, the method comprising:
   accessing a surgical plan for a corneal laser treatment of a cornea of a patient, wherein the surgical plan specifies position locations on the cornea for the corneal laser treatment, an ablation depth for each position location, and a number of laser pulses for each of the position locations; and
   performing the corneal laser treatment according to the surgical plan, wherein a thermal energy imparted to a first position location on the cornea by a first set of laser pulses is controlled by modulating an optical energy of the first set of laser pulses at the first position location to decrease a temperature of the cornea at the first position location, and wherein a thermal energy imparted to a second position location on the cornea by a second set of laser pulses is controlled by modulating an optical energy of the second set of laser pulses at the second position location to increase the temperature of the cornea at the second position location, wherein a number of laser pulses in the first set of laser pulses is less than a number of laser pulses in the second set of laser pulses.

2. The method of claim 1, wherein modulating the optical energy further comprises:
   modulating a frequency of the laser pulses.

3. The method of claim 1, wherein modulating the optical energy further comprises:
   modulating at least one of an amplitude and a duty cycle of the laser pulses.

4. The method of claim 1, wherein modulating the optical energy further comprises:
   linearly reducing the optical energy of the first set of laser pulses at the first position location from a rated value of a laser source used for the corneal laser treatment to a second value lower than the rated value over a duration, wherein the second value and the duration are predetermined to limit the thermal energy to prevent the temperature of the cornea at the first position location from exceeding a threshold temperature.

5. The method of claim 1, wherein modulating the optical energy further comprises:
   reducing the optical energy of the first set of laser pulses at first position locations from a rated value of a laser source used for the corneal laser treatment to a second value lower than the rated value, wherein the second value is predetermined to limit the thermal energy imparted to the first position locations to prevent the temperature of the cornea at the first position location from exceeding a threshold temperature, and wherein the first position locations are specified by the surgical plan to respectively receive the number of laser pulses exceeding a threshold pulse number.

6. The method of claim 5, wherein the second value further depends upon the number of laser pulses in a specified mathematical relationship.

7. The method of claim 1, wherein modulating the optical energy further comprises:
during the corneal laser treatment, measuring a maximum temperature of the cornea; and
based on the maximum temperature of the cornea, regulating the optical energy one of the first or second set of laser pulses at one of the first position location or the second position location to limit the thermal energy to prevent the maximum temperature from exceeding a threshold temperature, including reducing the optical energy when the maximum temperature exceeds the threshold temperature and increasing the optical energy when the maximum temperature does not exceed the threshold temperature.

8. The method of claim 7, wherein measuring the maximum temperature of the cornea further comprises:
measuring the maximum temperature of the stroma of the cornea.

9. The method of claim 7, wherein measuring the maximum temperature of the cornea further comprises:
using a thermal imaging device to generate temperature values correlated to the position locations; and
determining whether a local temperature at the first position location exceeds the threshold temperature.

10. The method of claim 9, wherein regulating the optical energy of the laser pulses at the first position location further comprises:
regulating the optical energy based on the local temperature at one of the first position location or the second position location, including reducing the optical energy when the local temperature exceeds the threshold temperature and increasing the optical energy when the local temperature does not exceed the threshold temperature.

11. A laser system for corneal laser treatments, the laser system comprising:
a laser source for generating laser pulses for a corneal laser treatment of a cornea of a patient;
a laser scanner enabled to receive the laser pulses from the laser source and direct the laser pulses to position locations on the cornea; and
a laser controller including a processor having access to memory media storing instructions executable by the processor for:
accessing a surgical plan for the corneal laser treatment, wherein the surgical plan specifies position locations on the cornea, an ablation depth for each position location, and a number of laser pulses for each of the position locations; and
controlling the corneal laser treatment according to the surgical plan, wherein a thermal energy imparted to a first position location on the cornea by a first set of laser pulses is controlled by modulating an optical energy of the first set of laser pulses at the first position location to decrease a temperature of the cornea at the first position location, and wherein a thermal energy imparted to a second position location on the cornea by a second set of laser pulses is controlled by modulating an optical energy of the second set of laser pulses at the second position location to increase the temperature of the cornea at the second position location, wherein a number of laser pulses in the first set of laser pulses is less than a number of laser pulses in the second set of laser pulses.

12. The laser system of claim 11, wherein modulating the optical energy further comprises:
modulating a frequency of the laser pulses.

13. The laser system of claim 11, wherein modulating the optical energy further comprises:
modulating at least one of an amplitude and a duty cycle of the laser pulses.

14. The laser system of claim 11, wherein modulating the optical energy further comprises:
linearly reducing the optical energy of the first set of laser pulses at the first position location from a rated value of a laser source used for the corneal laser treatment to a second value lower than the rated value over a duration, wherein the second value and the duration are predetermined to limit the thermal energy to prevent the temperature of the cornea at the first position location from exceeding a threshold temperature.

15. The laser system of claim 11, wherein modulating the optical energy further comprises:
reducing the optical energy of the first set of laser pulses at first position locations from a rated value of a laser source used for the corneal laser treatment to a second value lower than the rated value, wherein the second value is predetermined to limit the thermal energy imparted to the first position locations to prevent the temperature of the cornea at the first position location from exceeding a threshold temperature, and wherein the first position locations are specified by the surgical plan to respectively receive the number of laser pulses exceeding a threshold pulse number.

16. The laser system of claim 15, wherein the second value further depends upon the number of laser pulses in a specified mathematical relationship.

17. The laser system of claim 11, further comprising:
a thermal sensor configured to monitor thermal energy of the cornea, wherein modulating the optical energy further comprises:
during the corneal laser treatment, measuring a maximum temperature of the cornea using the thermal sensor; and
based on the maximum temperature of the cornea, regulating the optical energy of one of the first or second set of laser pulses at one of the first position location or the second position location to limit the thermal energy to prevent the maximum temperature from exceeding a threshold temperature, including reducing the optical energy when the maximum temperature exceeds the threshold temperature and increasing the optical energy when the maximum temperature does not exceed the threshold temperature.

18. The laser system of claim 17, wherein measuring the maximum temperature of the cornea further comprises:
measuring the maximum temperature of the stroma of the cornea.

19. The laser system of claim 17, wherein the thermal sensor includes a thermal imaging device, and wherein measuring the maximum temperature of the cornea further comprises:
using the thermal imaging device to generate temperature values correlated to the position locations; and determining whether a local temperature at the first position location exceeds the threshold temperature.

20. The laser system of claim 19, wherein regulating the optical energy of the laser pulses at the first position location further comprises:

regulating the optical energy based on the local temperature at one of the first position location or the second position location, including reducing the optical energy when the local temperature exceeds the threshold temperature and increasing the optical energy when the local temperature does not exceed the threshold temperature.

* * * * *